United States Patent [19]

Liotta et al.

[11] Patent Number: 4,565,789
[45] Date of Patent: Jan. 21, 1986

[54] CELL MATRIX RECEPTOR SYSTEM AND USE IN CANCER DIAGNOSIS AND MANAGEMENT

[75] Inventors: Lance A. Liotta, Bethesda, Md.; Nageswara C. Rao, Visiting Fellow, India; Victor Terranova, Gaithersburg, Md.

[73] Assignee: The United States of America as represented by the Department of Health and Human Services, Washington, D.C.

[21] Appl. No.: 481,934

[22] Filed: Apr. 4, 1983

[51] Int. Cl.[4] ................... G01N 33/566; G01N 33/50; G01N 33/534; G01N 33/567

[52] U.S. Cl. ................ 436/504; 260/112 R; 435/23; 435/69; 436/63; 436/501; 436/503; 436/519; 436/808; 436/813

[58] Field of Search .................. 260/112 R; 436/501, 436/503, 504, 519, 540, 808, 813

[56] References Cited

U.S. PATENT DOCUMENTS

| | | | |
|---|---|---|---|
| 4,298,590 | 11/1981 | Bogoch | 260/112 R |
| 4,334,017 | 6/1982 | Plotkin | 435/7 |
| 4,340,581 | 7/1982 | Timpl | 260/112 R |
| 4,383,985 | 5/1983 | Bartorelli | 260/112 R |

OTHER PUBLICATIONS

V. P. Terranova et al., Proc. Natl. Acad. Sci. USA, 80 (2), 444–448 (1983).
S. I. Rennard et al., Anal. Biochem., 104 (1), 205–214 (1980).
J. Risteli et al., Anal. Biochem., 113 (2), 372–378 (1981).
C. N. Rao et al., I, Arch. Biochem. Biophys., 219 (1), 65–70 (1982).
C. N. Rao et al., II, J. Biol. Chem., 257 (16), 9740–9744 (1982).

Primary Examiner—Sidney Marantz
Attorney, Agent, or Firm—Holman & Stern

[57] ABSTRACT

A cell matrix receptor specific for laminin expressed on the surface of carcinoma and epithelial cells is provided. The binding of these cells to extracellular matrix is mediated by the laminin molecule, which has binding domains for type IV collagen of the matrix and the cell surface receptor. Fragments of the laminin molecule lacking the type IV collagen binding domain and antibodies to the receptor are useful in conjunction with the cell receptor as ligands in binding assays for cancer diagnosis and in cancer management.

26 Claims, 15 Drawing Figures

FIG. 1. STRUCTURAL AND FUNCTIONAL PROPERTIES OF LAMININ AND ITS FRAGMENTS. CIRCLES REPRESENT GLOBULAR END REGIONS. REPRESENTATIVE ELECTRON MICROGRAPHS OF LAMININ OR PURIFIED FRAGMENTS ARE SHOWN.

| MOLECULE | STRUCTURE | BINDING CAPACITY |
|---|---|---|
| NATIVE LAMININ | 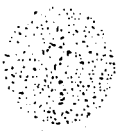 | CELL SURFACE RECEPTOR TYPE IV COLLAGEN HEPARIN SULFATE PROTEOGLYCAN |
| a3 FRAGMENT |  | CELL SURFACE RECEPTOR TYPE IV COLLAGEN |
| C1 FRAGMENT |  | CELL SURFACE RECEPTOR |
| P1 FRAGMENT |  | CELL SURFACE RECEPTOR |

FIG. 1

FIG. 1. STRUCTURAL AND FUNCTIONAL PROPERTIES OF LAMININ AND ITS FRAGMENTS. CIRCLES REPRESENT GLOBULAR END REGIONS. REPRESENTATIVE ELECTRON MICROGRAPHS OF LAMININ OR PURIFIED FRAGMENTS ARE SHOWN.

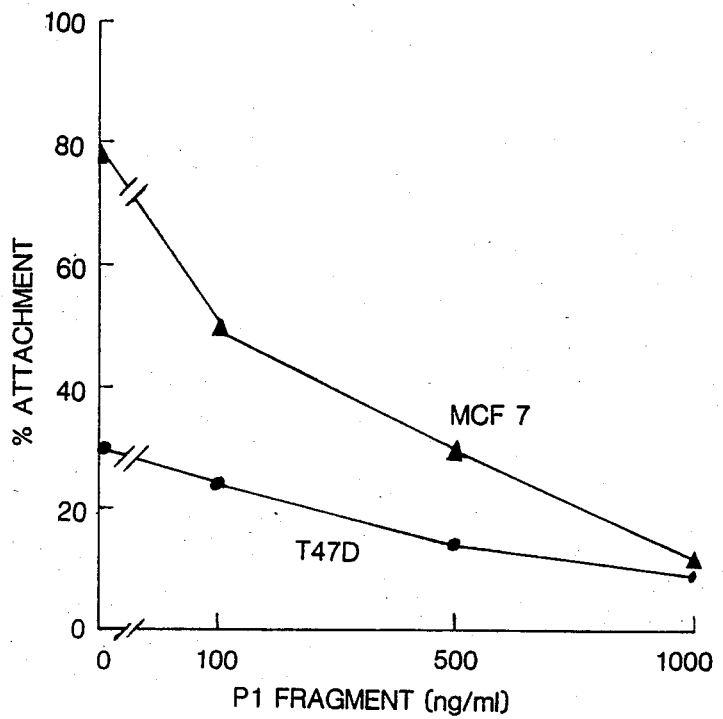

FIG. 2

FIG. 2. COMPETITION OF P1 FRAGMENT AND NATIVE LAMININ IN MEDIATING ATTACHMENT: DOSE-RESPONSE CURVE FOR P1 ($M_R$ 280,000) FRAGMENT-MEDIATED INHIBITION OF LAMININ-MEDIATED ATTACHMENT OF MCF-7 AND T47-D CELLS TO TYPE IV COLLAGEN-COATED DISHES. CELLS WERE INCUBATED FOR 3 HR WITH NATIVE LAMININ AT 0.5μG/ML AT THE START OF THE EXPERIMENT AND HARVESTED AS DESCRIBED. DATA POINTS REPRESENT MEAN OF TRIPLICATE ASSAYS NOT DIFFERING BY MORE THAN 8%.

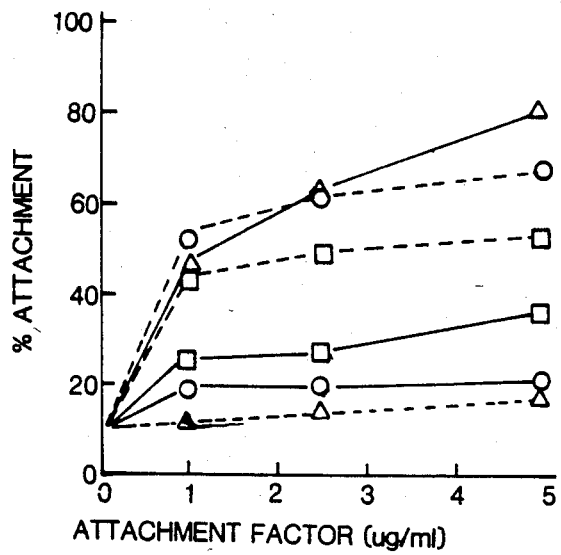

FIG. 3

FIG. 3. DOSE-RESPONSE CURVE FOR LAMININ MEDIATED ATTACHMENT OF MCF-7 (△), ZR-75 (□), AND T47-D (○) CELLS TO TYPE IV COLLAGEN-COATED DISHES AND FIBRONECTIN MEDIATED ATTACHMENT OF MCF-7 (△), ZR-75-1 (□), AND T47-D (○) CELLS TO TYPE I COLLAGEN-COATED DISHES. CELLS WERE PRETREATED FOR 4 HR IN RPMI 1640 MEDIUM WITH 10% FETAL BOVINE SERUM CONTAINING CYCLOHEXIMIDE AT 25μG/ML. AFTER INCUBATION THE CELLS WERE TRYPSINIZED, WITH 0.01% TRYPSIN/0.1% EDTA, CENTRIFUGED (1,000 FOR 5 MIN.) AND RESUSPENDED IN SERUM-FREE DULBECCO'S MODIFIED EAGLE'S MEDIUM CONTAINING CYCLOHEXIMIDE AT 25μG/ML. THE CELLS WERE THEN INCUBATED FOR 3 HR IN THE PRESENCE OF THE INDICATED CONCENTRATIONS OF EITHER FIBRONECTIN OR LAMININ. THE ATTACHED CELLS WERE REMOVED BY TRYPSINIZATION AND COUNTED ELECTRONICALLY. DATA POINTS REPRESENT THE MEAN OF TRIPLICATES NOT DIFFERING BY MORE THAN 10%. FIBRONECTIN DID NOT MEDIATE THE ATTACHMENT OF MCF-7 CELLS TO TYPE IV COLLAGEN. LAMININ DID NOT MEDIATE ATTACHMENT OF T47-D CELLS TO TYPE 1 COLLAGEN.

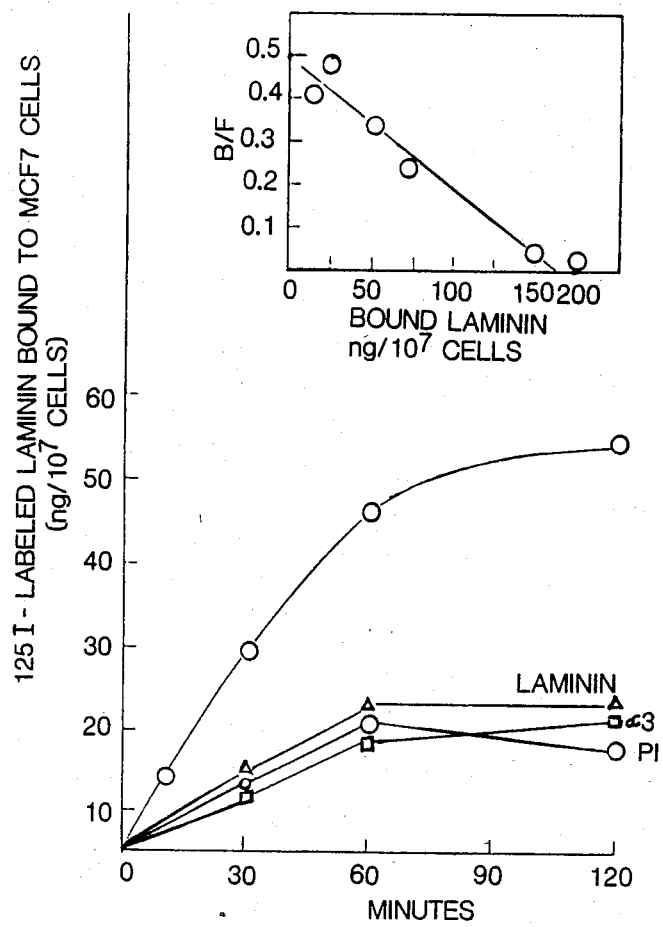

FIG. 4

FIG. 4. BINDING OF 125 LAMININ TO MCF-7 HUMAN BREAST CARCINOMA CELLS. A TIME COURSE OF BINDING IS SHOWN WITH OR WITHOUT 100x COMPETITION BY UNLABELED LAMININ OR PURIFIED UNLABELED PROTEASE DERIVED FRAGMENTS OF LAMININ. O, TOTAL LAMININ BINDING WITH NO COMPETITOR; △, UNLABELED LAMININ; □, $\alpha$-3, $M_R$ 600,000 $\alpha$-THROMBIN DIGEST FRAGMENT OF LAMININ; O, $P_L$ PEPSIN FRAGMENT OF LAMININ. (INSET) SCATCHARD PLOT OF THE 125-I-LAMININ BINDING TO THE MCF-7 CELLS. A LEAST-SQUARES ANALYSIS FOR THE DATA SHOWN YIELDED AN R VALUE OF 0.98 FOR A LINEAR FIT. THE MCF-7 CELLS WERE INCUBATED WITH A SERIES OF CONCENTRATIONS OF 125 I-LAMININ FOR 90 MIN. THE AMOUNT OF LAMININ BOUND TO THE MCF-7 CELL SURFACE IS SHOWN ON THE ABSCICCA. THE RATIO OF BOUND TO FREE LAMININ IS SHOWN ON THE ORDINATE. BINDING AFFINITY OF THE ISOLATED LAMININ RECEPTOR ($M_R$ 60,000 -75,000) WAS SIMILAR TO THAT SHOWN HERE FOR WHOLE CELLS.

FIG. 5. COMPARISON OF THE TIME COURSE OF TOTAL 125 I-LAMININ BINDING TO MCF-7 BREAST CARCINOMA (▲), T47-D BREAST CARCINOMA (○), AND HUMAN FIBROBLAST CRL 1507 AND 1477 (▽) (NOTE: DATA ARE SHOWN FOR CRL 1507 CELLS; DATA FOR CRL 1477 CELLS WERE IDENTICAL.)

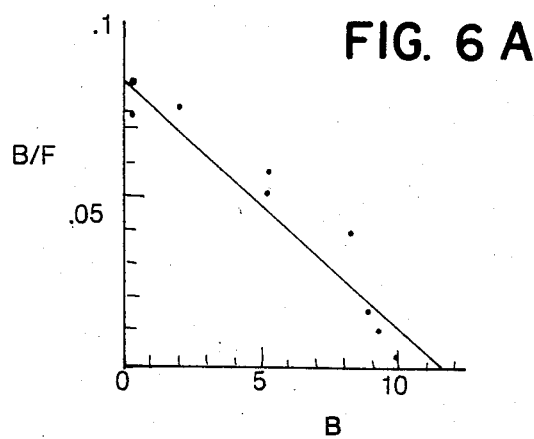

FIG. 6 A

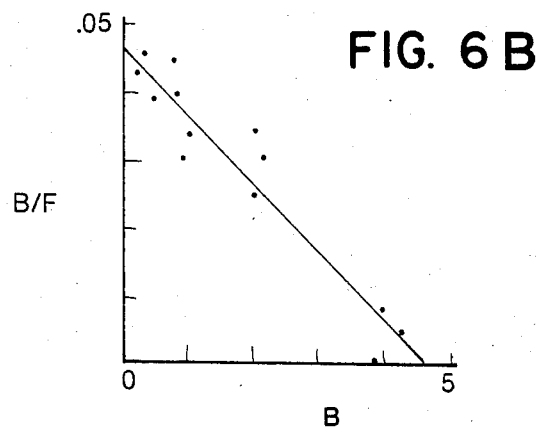

FIG. 6 B

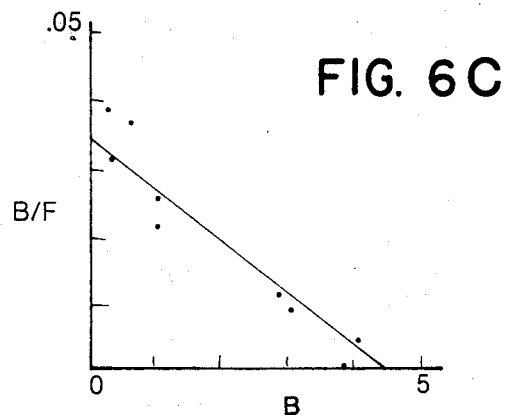

FIG. 6 C

FIG. 6: SCATCHARD ANALYSIS FOR THE SPECIFIC BINDING OF LAMININ TO SUSPENDED BL6 MELANOMA CELLS (PANEL A), DETERGENT EXTRACT OF THE BL6 PLASMA MEMBRANES (PANEL B) AND ISOLATED LAMININ RECEPTOR (PANEL C). FOR PANEL A THE X-AXIS UNITS ARE LAMININ (NG/ML) AND THE X INTERCEPT IS 11.3; KD = 2.2 NM, R = 0.94. FOR PANEL B THE X-AXIS UNITS ARE PLASMA MEMBRANE PROTEIN (FM/MG PROTEIN). THE X INTERCEPT IS 4.6, KD = 1.5 NM, R = 0.95. FOR PANEL C THE X-AXIS UNITS ARE LAMININ (NM) AND THE X INTERCEPT IS 4.46, KD = 2.0 NM, R = 0.95. THE ISOLATED RECEPTOR USED IN THIS BINDING ASSAY IS SHOWN IN FIG. 8.

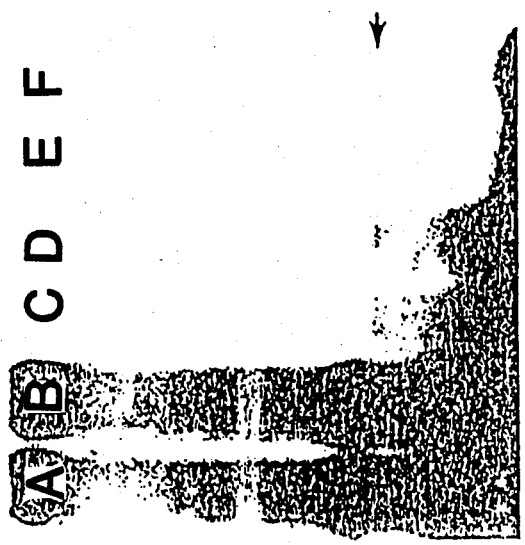

FIG. 7: SDS (7%) GEL ELECTROPHORESIS AUTORADIOGRAPHY DEMONSTRATING BINDING OF SOLUBILIZED 125 I-LABELED BL6 PLASMA MEMBRANE EXTRACT TO LAMININ IMMOBILIZED ON SEPHAROSE 4B. A: PLASMA MEMBRANE EXTRACT. B: SUPERNATE FRACTION OF EXTRACT UNBOUND TO LAMININ-SEPHAROSE C AND D: REPLICATE PELLET FRACTION OF EXTRACT BOUND TO LAMININ-SEPHAROSE. E: PELLET FRACTION AFTER COMPETITION WITH (250 X) UNLABELED PLASMA MEMBRANE EXTRACT. F: PELLET FRACTION AFTER COMPETITION WITH LAMININ (250 X) IN SOLUTION. A SINGLE MAJOR COMPONENT (DENOTED WITH THE ARROW) BINDS TO THE SOLID PHASE LAMININ AND IS REMOVED BY COMPETITION.

FIG. 8

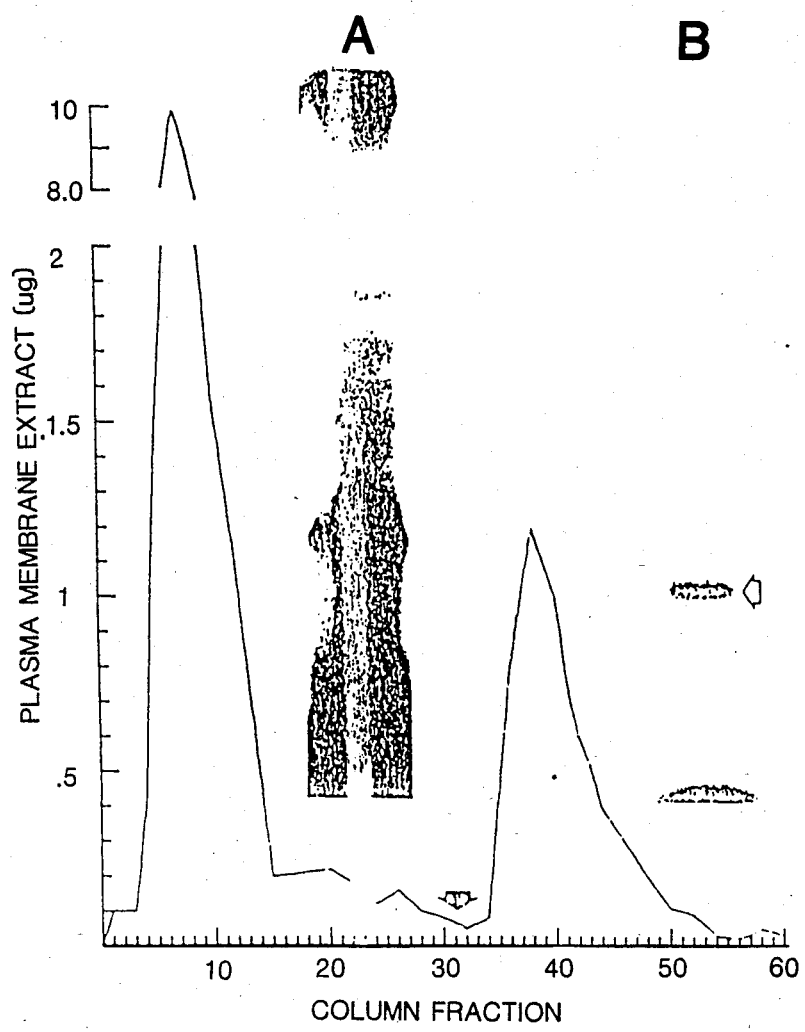

FIG. 8: ISOLATION OF LAMININ RECEPTOR USING LAMININ AFFINITY CHROMATOGRAPHY. THE BL6 PLASMA MEMBRANE EXTRACT WAS APPLIED TO THE AFFINITY COLUMN AND THE BOUND RECEPTOR WAS ELUTED (SOLID ARROW) WITH 0.2 M GLYCINE, pH 3.5. THE UNBOUND FRACTION (95%) IS THE FIRST PEAK. GEL ELECTROPHORESIS FOLLOWED BY AUTORADIOGRAPHY OF THE UNBOUND FRACTION REVEALS A LARGE SERIES OF COMPONENTS (LANE A). THE BOUND FRACTION AFTER ELUTION MIGRATED AS A SINGLE BAND (OPEN ARROW) ON POLYACRYLAMIDE GEL ELECTROPHORESIS (LANE B) WITH A $M_R$ OF 67,000 AFTER REDUCTION.

FIG. 9: TISSUE COURSE OF 125-I-LAMININ BINDING TO HUMAN BREAST CARCINOMA PLASMA MEMBRANES AT 25°C. THE PLATEAU OF BINDING IS REACHED BY ONE HOUR. WITH THE ADDITION OF COLD LIGAND RAPID DISPLACEMENT IS NOTED. THE ERROR BARS INDICATE THE RANGE OF QUADRUPLICATE ASSAYS FROM 10 POOLED PATIENT SAMPLES.

FIG. 10: SCATCHARD ANALYSIS OF SPECIFIC LAMININ BINDING TO HUMAN BREAST CARCINOMA PLASMA MEMBRANES. R = 0.85. THE KD IS IN THE RANGE OF 2NM.

FIG. 11: LAMININ FRAGMENTS. THE GEL ELECTROPHORESIS PATTERN OF THE PURIFIED FRAGMENTS IS SHOWN BELOW AND THE ELECTRON MICROSOPIC IMAGE OF THE MOLECULES ARE SHOWN ABOVE.

A: WHOLE LAMININ.
B: FRAGMENT ALPHA WHICH IS MISSING THE LONG ARM.
C: FRAGMENT C1 WHICH IS MISSING BOTH THE LONG ARM AND THE GLOBULAR END REGIONS OF THE SHORT ARMS.

CELL MATRIX RECEPTOR SYSTEM AND USE IN CANCER DIAGNOSIS AND MANAGEMENT

BACKGROUND OF THE INVENTION

The basement membrane is a ubiquitous, specialized type of extracellular matrix separating organ parenchymal cells from interstitial collagenous stroma. Interaction of cells with this matrix is an important aspect of both normal and neoplastic cellular processes. Normal cells appear to require an extracellular matrix for survival, proliferation, and differentiation, while migratory cells, both normal and neoplastic, must traverse the basement membrane in moving from one tissue to another. In particular, metastatic cancer cells arising in squamous or glandular epithelium must traverse the basement membrane to enter the circulatory and lymphatic systems (intravasation); the circulating neoplastic cells are typically arrested in the capillary beds of an organ, invade the blood vessel walls, and penetrate the basement membrane to extravascular tissue (extravasation), where a secondary neoplasm is then established. The mechanisms of cellular interaction with the basement membrane are thus of great interest.

The interaction of cells with extracellular matrices is dependent upon the ability of the cells to attach themselves to the matrix; it is known that this attachment may be mediated by specific glycoproteins which typically bind cells to discrete collagen types present in the matrix. Fibronectin-mediated attachment of fibroblasts, myoblasts, and smooth muscle cells to interstitial type I and type III collagen, and chondronectin-mediated attachment of chondrocytes to type II cartilage collagen, are exemplary.

It has been found that the attachment of both normal and neoplastic cells to the basement membranes is similarly mediated. The primary constituents of the basement membrane are type IV collagen, glycoproteins. and proteoglycans. The glycoprotein laminin mediates the attachment of both epithelial and neoplastic calls to the basement membrane, binding the cells to type IV collagen by mechanisms to be described hereinafter. Since, as previously noted, metastasizing tumor cells must traverse basement membranes at multiple stages in the metastatic process, and since the first step in this process is tumor cell attachment to the basement membrane, the elucidation of this mechanism and the corollary characterization of specific attachment factors which promote or inhibit tumor cell attachment to this membrane has important implications for cancer diagnosis and management.

SUMMARY OF THE INVENTION

Methods for the diagnosis and management of cancer according to the invention have been predicated on the successful isolation and purification of a unique cell matrix receptor for laminin, and the characterization of substrate-specific binding site domains on the laminin molecule. Isolation of these domains according to substrate on protease-derived laminin fragments permits selection of fragments having specific binding capacities, since each fragment contains at least one, but not all, of the domains present on the intact molecule. Of particular interest are fragments which retain only binding sites for the cell matrix receptor. This receptor, which has a high affinity for receptor binding domains in the laminin molecule, is characteristic of human cancer cells and perhaps epithelial cells. The receptor is present on the surface of these cells, and can be isolated from plasma membrane extracts.

Bioassays based on this model within the scope of the invention include immunoassays, especially prognostic radioimmunoassays, applied to clinical specimens for the detection and quantitation of laminin cell receptors expressed by metastasizing cells, or for the isolation of highly metastatic tumor cells from a mixed population. Therapeutic procedures include the treatment of hosts with laminin fragments agonistic or antagonistic to the laminin molecule to block attachment of tumor cells to type IV collagen and reduce hematogenous formation of metastases. Suitable laminin fragments may also be used as ligands for known or experimental chemotherapeutic agents; the conjugation of toxins with these fragments permits direct introduction of the conjugate to the metastasizing tumor cell for in vivo treatment of cancer, or for drug evaluation in vivo or in vitro. The described model is also useful in the evaluation of synthetic binding site analogues for therapeutic use in cancer management. Other proposed therapeutic uses include the use of laminin or appropriate laminin fragments to promote cell adhesion to type IV collagen, for example to promote adhesion and growth of epithelial cells in burn therapy. These fragments, and laminin itself, may broadly act as a growth factor on receptive cells, promoting cell attachment and dispersion, and stimulating cell division.

BRIEF DESCRIPTION OF DRAWINGS

FIG. 1 describes structural and functional properties of laminin and its fragments. Circles represent globular end regions. Representative electron micrographs of laminin or purified fragments are shown.

FIG. 2 shows competition of P1 fragment and native laminin in mediating attachment: dose-response curve for P1 ($M_R 280,000$) fragment-mediated inhibition of laminin-mediated attachment of MCF-7 and T47-D cells to type IV collagen-coated dishes. Cells were incubated for 3 hr with native laminin at 0.5 $\mu$g/ml at the start of the experiment and harvested as described. Data points represent mean of triplicate assays not differing by more than 8%.

FIG. 3 shows dose-response curve for laminin mediated attachment of MCF-7 ($\Delta$), ZR-75 ($\square$), and T47-D ( $\bigcirc$ ) cells to type IV collagen-coated dishes and fibronectin mediated attachment of MCF-7 ($\Delta$), ZR-75-1 ($\square$), and T47-D ( $\bigcirc$ ) cells to type I collagen-coated dishes. Cells were pretreated for 4 hr in RPMI 1640 medium with 10% fetal bovine serum containing cycloheximide at 25 $\mu$g/ml. After incubation the cells were trypsinized, with 0.01% trypsin/0.1% EDTA, centrifuged (1,000 for 5 min.) and resuspended in serum-free Dulbecco's modified Eagle's medium containing cycloheximide at 25 $\mu$g/ml. The cells were then incubated for 3 hr in the presence of the indicated concentrations of either fibronectin or laminin. The attached cells were removed by trypsinization and counted electronically. Data points represent the mean of triplicates not differing by more than 10%. Fibronectin did not mediate the attachment of MCF-7 cells to type IV collagen. Laminin did not mediate attachment of T47-D cells to type 1 collagen.

FIG. 4 shows binding of 125 Laminin to MCF-7 human breast carcinoma cells. A time course of binding is shown with or without 100x competition by unlabeled laminin or purified unlabeled protease derived fragments of laminin, ○, Total laminin binding with no competitor; △, unlabeled laminin; □, α-3, $M_R$ 600,000 α-thrombin digest fragment of laminin; ○, PL pepsin fragment of laminin. (Inset) Scatchard plot of the 125-I-Laminin binding to the MCF-7 cells. A least-squares analysis for the data shown yielded an R value of 0.98 for a linear fit. The MCF-7 cells were incubated with a series of concentrations of 125 I-Laminin for 90 min. The amount of laminin bound to the MCF-7 cell surface is shown on the abscicca. The ratio of bound to free laminin is shown on the ordinate. Binding affinity of the isolated laminin receptor ($M_R$ 60,000–75,000) was similar to that shown here for whole cells.

FIG. 6 shows scatchard analysis for the specific binding of laminin to suspended BL6 melanoma cells (panel A), detergent extract of the BL6 plasma membranes (panel B) and isolated laminin receptor (panel C). For panel A the X-axis units are laminin (ng/ml) and the X intercept is 11.3; KD=2.2 nm, R=0.94. For panel B the X-axis units are plasma membrane protein (fm/mg protein). The X intercept is 4.6, KD=1.5 nm, R=0.95. For panel C the X-axis units are laminin (nm) and the X intercept is 4.46, KD=2.0 nm, R=0.95. The isolated receptor used in this binding assay is shown in FIG. 8.

FIG. 8 shows isolation of laminin receptors using laminin affinity chromatography. The BL6 plasma membrane extract was applied to the affinity column and the bound receptor was eluted (solid arrow) with 0.2M clycine, pH 3.5. the unbound fraction (95%) is the first peak. Gel electrophoresis followed by autoradiography of the unbound fraction reveals a large series of components (lane A). The bound fraction after elution migrated as a single band (open arrow) on polyacrylamide gel electrophoreis (lane b) with a $M_R$ of 67,000 after reduction.

DETAILED DESCRIPTION OF THE INVENTION

Figure 5:
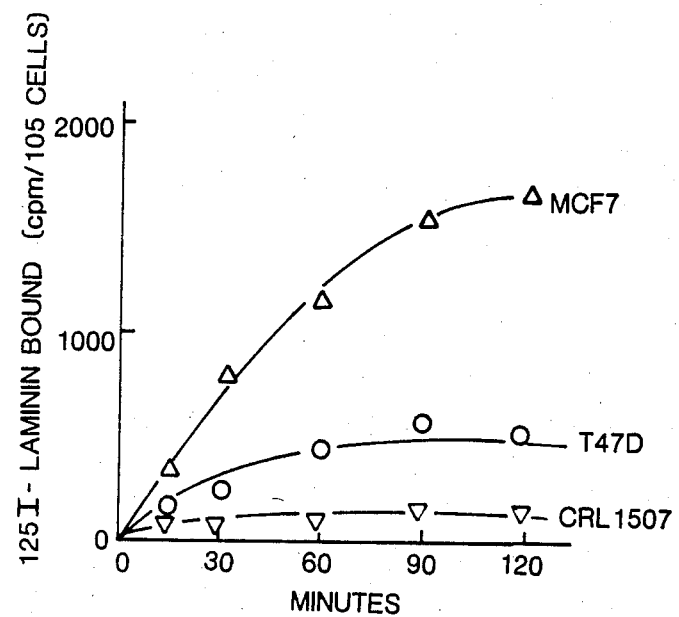
FIG. 5 shows comparison of the time course of total 125 I-laminin binding to MCF-7 breast carcinoma (△), T47-Dbreast carcinoma (○), and human fibroblast CRL 1507 and 1477 (∇) (Note: data are shown for CRL 1507 cells; data for CRL 1477 cells were identical).

The glycoprotein laminin is uniquely localized in the basement membranes and is the major glycoprotein constituent thereof. While cells bearing the laminin receptor are capable of directly attaching to the basement membrane laminin component, the preferred pathway of invading cells is by laminin-mediated attachment to the type IV collagen constituent of the basement membrane. The secretion of laminin by metastasizing cells facilitates the invasion process.

Laminin ($M_r 10^6$) upon reduction migrates on polyacrylamide gels as two subunits with apparent molecular weights of 200,000 (α3 subunit) and 400,000 (β subunit). Electron microscopy techniques have demonstrated that the configuration of the laminin molecule is that of a Latin cross having one long arm (77 nm) and three identical short arms (37 nm). The three short arms of the cross comprise the α3 subunit, comsisting of 3 similar ($M_r$ 200,000) chains, while the long arm of the cross comprises the β subunit ($M_r$ 400,000); all arms have globular end units.

Laminin binds with high affinity to the cell matrix receptor ($K_d=2$ nm), to type IV collagen, and also to heparin. According to the invention, substrate-specific binding domains residing on distinct regions of the molecule were characterized by cell attachment and collagen-binding assays using enzyme digestion products of laminin. Digestion of the molecule with α-thrombin, pepsin, and cathepsin G yielded fragments having more limited binding capacity than that exhibited by native laminin. Structural properties of native laminin and these fragments are shown in FIG. 1. The α3 fragment ($M_r$ 600,000) derived from α-thrombin digestion of laminin lacks the long arm ($M_r$ 400,000) fragment of the molecule, and retains the short arms with their globular end regions. Digestion of laminin with pepsin or cathepsin G yields P1 ($M_r$ 280,000) and C1 ($M_r$ 350,000) fragments, respectively, wherein the long arm of the molecule is removed and also the globular end regions of the short arms are altered. Functional properties of native laminin and the α3, C1 and P1 fragments are summarized in FIG. 1 and Table 1. C1 and P1 fragments having similar molecular weights and binding capacities are also obtained by digestion of laminin with plasmin and chymotrypsin.

TABLE I

Ability of laminin and laminin fragments to bind to type IV collagen and to mediate human breast carcinoma cell adhesion to type IV collagen.

| Laminin or fragment | % binding to collagen | % attachment MCF-7 | % attachment T47-D |
|---|---|---|---|
| Laminin | 80 | 84 | 28 |
| α3 | 85 | 81 | 29 |
| P1 | 15 | 13 | 11 |
| C1 | 10 | 11 | 10 |
| None | — | 48 | 22 |

Binding of whole laminin or purified protease-derived fragments of laminin to procollagen type IV immobilized on nitrocellulose was measured.

Ten micrograms of the ligand was applied to 25 μg of type IV collagen. Percent attachment of MCF-7 and T47-D cell to type IV collagen substrate in the presence of various laminin fragments is indicated. Freshly trypsinized cells were incubated for 3 hrs. in serumfree Dulbecco's modified Eagle's medium with laminin added at 1 μg/ml, $M_r$ 600,000 α3 laminin fragment at 1 μg/ml, P1 laminin fragment at 100 μg/ml, or C1 laminin fragment at 100 μg/ml. Unattached cells were removed and counted, the dishes were washed with $P_1$/NaCl, and the attached cells were removed with 0.01% trypsin/0.1% EDTA and counted electronically. The data are the mean of quadruplicates with a range less than 10% of the mean; sensitivity was as low as 100 ng/ml.

Digestion of laminin with α-thrombin does not affect the binding capacity of the α3 fragment for the cell matrix receptor or type IV collagen. The P1 or C1 fragments are not capable of mediating attachment of human breast carcinoma cell lines to type IV collagen (Table 1), while the α3 fragment is comparable to native laminin in its mediating ability: both stimulate attachment. As seen in FIG. 2, the P1 fragment blocks attachment of human breast carcinoma cells to type IV collagen; the C1 fragment also blocks attachment of carcinoma cells to type IV collagen, completely inhibiting attachment of MCF-7 cells to type IV collagen when used in concentrations of 1 μg/ml in a similar protocol (data not given). For comparison, a dose-response curve for laminin-mediated attachment of human carcinoma cells is shown in FIG. 3; while fibronectin mediated attachment of the cells to type I collagen, laminin in the same dose range failed to stimulate attachment of the cells to type I collagen (data not shown). Normal binding capacities of the cell lines employed for types I and IV collagen in the absence of specific attachment factors is summarized in Table 2.

TABLE II

| Attachment of human breast carcinoma cells | | |
|---|---|---|
| | % attachment | |
| Cells | Type I | Type IV |
| MCF-7 | 22 | 68 |
| ZR-75-1 | 54 | 44 |
| T47-D | 62 | 33 |

Attachment of cells to types I and IV collagen-coated dishes was measured after 3-hrs incubation in serum-free Dulbeccos' modified Eagle's medium. Attachment assay is detailed in the legend to FIG. 3. The data are the means of quadruplicates, which did not differ by more than 5%.

The binding domains present on the laminin molecule were accordingly characterized and mapped as illustrated in FIG. 1. The cell matrix receptor present on the cell surface binds to a protease-resistant, disulfide bonded intersection region of the three short arms of the laminin molecule. The type IV collagen-binding domain resides on or near the globular regions of the short arms, while the long arm of the molecule binds to heparin sulfate proteoglycan. Since the α3 fragment retains both the cell-binding and collagen-binding domains, this fragment exhibits a mediating capability similar to that of the intact molecule. The removal of the globular regions of the short arms by pepsin or cathepsin G eliminates the binding domains for type IV collagen, and the corresponding fragments thus lack the ability to mediate cell attachment to the basement membrane. The P1 and C1 fragments, however, retain the cell receptor binding domains, and are thus able to saturate the receptors in successful competition with native laminin.

Isolation and purification of the cell matrix receptor was accomplished by detergent extraction from plasma membranes and purification using laminin affinity chromatography. The purified receptor has a molecular weight of about 50,000 to about 75,000 (SDS polyacrylamide gel electrophoresis) and retains a high binding affinity for laminin ($K_d$=2 nm) close to that of the plasma membranes or whole cells. The receptor has been identified on both human and murine tumor cells.

Diagnostic assays for cells bearing the receptor moiety such as human cancer cells, especially carcinoma cells have been developed which are contemplated as useful in the diagnosis and prognosis of cancer, based on clincal specimens such as tissue or cytological biopsies. In general, known binding assays of the immunoassay type are useful, such as radioimmunoassays or enzyme immunoassays employing as labelled ligand laminin, appropriate laminin fragments retaining biologically active cell receptor sites, or antibodies raised in heterologous species animals such as rabbit or goat against purified cell receptor, or monoclonal antibodies having the desired affinity and specificity characteristics. Typical assays include conventional competitive binding assays on plasma membrane extracts of the cell receptors, employing immobilized ligand or receptor. Diagnostic kits for performing these binding assays are within the scope of the invention and include, for example, free or immobilized radiolabelled laminin or laminin fragment, or if antibody is employed, sandwich-type kits including, for example, bound labelled antibody and anti-antibody. Results are suitable evaluated by Scatchard analysis of the specific binding (Scatchard, *Ann. N.Y. Acad. Sci.* 51: 660–672, 1949) of the specimen, and comparison with binding affinity of cultured carcinoma cells of the relevant type. Scatchard binding analysis of human breast carcinoma cells indicate as estimated $K_d$ of 50–2.2 nm for metastasizing carcinoma (MCF-7) cells, with calculations suggesting about 10,000 to 100,000 receptors per cell for all types of carcinoma. In contrast, no specific binding was found by Scatchard analysis in samples of mammary fibrosclerosis tissue containing no neoplastic cells.

Laminin fragments containing cell receptor binding sites but devoid of type IV collagen binding domains (P1 and C1), in addition to being useful in diagnostic binding assays, are contemplated as useful in the treatment of cancer to inhibit formation of metastases. In in vitro mouse studies, fragments blocked attachment of BL6 murine melanoma cells to type IV collagen in the presence of exogenous laminin. The C1 fragment, when preincubated with BL6 melanoma cells, markedly inhibited or abolished hematogenous metastases formation in vivo on a dose dependent basis. Further, the fragments are non-toxic, with no evidence of adverse immunogenic side effects in experimental animals. In addition, such fragments are useful in targeting effective chemotherapeutic agents, or as carriers for known effective anti-tumor drugs. By conjugation of the drug with the ligand, toxic agents can be localized on the surface of invasive tumor cells; drugs such as ricin may be conjugated to the ligand by known methods, such as those used to conjugate such drugs to antibodies for tumor-associated antigens.

The concepts of the present invention have implications for a variety of biological processes including cell differentiation, mitogenesis, morphogenesis, and neoplasia. The methods described herein are in part predicated on the hypothesis that in all benign neoplasms and in carcinoma in situ, the basement membrane remains a continuous structure, and that, in the case of benign cells, the laminin receptors are occupied by attachment to the basement membrane. A hallmark of invasive cancer, however, is an absence of a formed basement membrane adjacent invading tumor cells; thus, the invading tumor cells may contain a large number of laminin receptors which are expressed on the cell surface, but are not bound to ligand, in contrast to epithelial cells, or benign neoplasms. The unique availability of laminin receptor sites on metastasizing carcinoma cells may thus prove to be a important concept in cancer management and diagnosis.

EXAMPLES

The concepts exemplified are elaborated in the following publications, incorporated herein by reference: Terranova, et al., *Proc. Natl. Acad. Sci.*, 80: 444–448 (1983); and Rao, et al., *J. Biol. Chem.*, 257: 9740–9744 (Aug. 1982).

EXAMPLE 1

Preparation of Laminin Fragments

A. Materials and Methods.

1. Purified α thrombin was kindly supplied by John W. Fenton (N.Y. Dept. of Health, Albany). Digestion with α thrombin was performed at pH 7.6 and 25° C. using an enzyme to substrate weight ratio of 1:100 as described in *Thromb. Res.*, 21: 663–673. Thrombin digestion was arrested by addition of a 2-fold excess of hirudin (Sigma). Laminin digestion with pepsin, a thrombin, and cathepsin G was performed as described in Cancer Res., 41: 4629–4636 (1981); *Hoppe-Seyler's Z. Physiol. Chem.*, 361: 1651–1660 (1980); *J. Mol. Biol.*, 257: 9740–9744 (1982), and *Arch. Biochem. Biophys.*, 219: 65–70 (1982). Laminin digestion with chymotrypsin and plasmin is similarly described in these publications, which are incorporated herein by reference.

2. Chymotrypsin was purchased from Worthington Biochemicals. Plasmin was a gift from Dr. G. Murano, Bureau of Biologies, NIH. Cathepsin G purified from human polymorphonuclear leukocytes was generously supplied by Dr. Norman Schechter (Department of Dermatology, Duke University, N.C.). Aliquots of laminin (corresponding to 40 μg) were incubated with α-thrombin, at 25° C., at an enzyme to substrate ratio of 1:100 (w/w). The digestion reaction was stopped by the addition of excess hirudin (Sigma). Digestions with plasmin, cathepsin G, and chymotrypsin in presence or absence of hirudin were performed at 25° C. and enzyme to substrate ratio was maintained at 1:50 (w/w). Digestion reaction with plasmin was arrested by the addition of a fivefold excess of aprotinin (Sigma). Incubations with cathepsin G and chymotrypsin were stopped by the addition of excess amounts of PMSF[2] (Sigma) and TPCK (Sigma) respectively.

3. Laminin was purified from 0.5M NaCl extracts of mouse EHS tumor by DEAE cellulose and agarose A 5M column chromatography and stored frozen in phosphate-buffered saline.

4. Digestion products are identified by electrophoresis on 3.5 or 5% polyacrylamide slab gels according to the method of Laemmli, except that 0.5M urea was added for better band resolution. In brief, the proteins are ethanol precipitated, dissolved in sample buffer containing 7.5mM dithiothreitol (DTT, Biorad Laboratories), heat denatured (95° C., for 3 min.), and applied onto the wells of a 3% stacking gel. The electrophoresis was performed at 25 MA/slab and the proteins were stained with Coomassie brilliant blue R250.

5. Column chromatography. One to two milligrams of complete digests of laminin by cathepsin G was dialyzed overnight at 4° C. against 0.2M ammonium bicarbonate pH 7.8 and then applied to a 30-cm TSK 3000 SW high-performance (HPLC) liquid chromatography gel filtration column (Altex, Beckman Instruments, Berkeley, Calif.) previously equilibrated with the same buffer. The column was eluted with a flow rate of 0.5 ml/min at 500 PSI using a Waters HPLC chromatography pump and fractions of 1 ml were collected. The laminin fragment which upon reduction migrated as two polypeptides of 160,000 and 130,000M, was eluted in the void volume.

6. Electron microscopy. The method of Engel et al. (J. Mol. Biol. 150: 97–120(1981)), was followed for the visualization of laminin or the fragment of laminin purified after protease digestion. The protein was made up to 25 μg/ml in a buffer containing 60% glycerol, and 0.2M ammonium acetate pH. 7.4 and sprayed onto freshly cleaved mica discs using a nebulizer. The samples were shadowed with platinum/palladium followed by carbon in an evacuated chamber (Ladd vacuum evaporator $2\times10^5$ Torr) at angles of 8:1 and 8:13, respectively, and rotation speed at medium setting. The replicas were floated onto distilled water, placed upon 150 mesh grids, and viewed in Philips electron microscope 201 at 60 kV. The length of different arms of the individual molecules was measured with a Hewlett-Packard digitizer. (Fort-Collins, Colo.). Each individual arm was measured starting from the common intersection point of the four arms and including the globular end regions.

Protease fragments were isolated by HPLC (Beckman) and studied by SDS gel electrophoresis on 5% polyacrylamide slab gels, as described in Terranova, et al. and Rao, et al., supra. The P1 fragments obtained by digestion of laminin with plasmin or pepsin and the C1 fragments obtained by digestion of laminin with chymotrypsin or cathepsin G are characterized in the references noted in Example (A), supra. The α3 fragment is similarly characterized.

The digestion products of laminin produced by cathepsin G, chymotrypsin, and plasmin were compared after first digesting laminin with α-thrombin as reported in *Cancer Res.* 41: 4629–4636, 1981. The major digestion products produced after the sequence of two digestions were identical in size and amount to those fragments produced by directly digesting whole laminin. Without reduction these two fragments by all three proteases migrated as a single broad band on 3.5% polyacrylamide gel (not shown).

Figure 11:
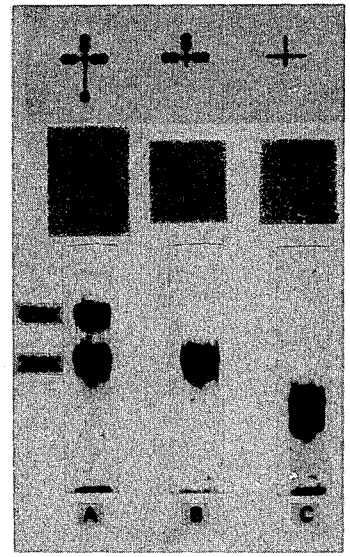
FIG. 11 shows laminin fragments. The gel electrophoresis pattern of the purified fragments is shown below and the electron microscopic image of the molecules are shown above.
A: Whole Laminin.
B: Fragment alpha which is missing the long arm.
C: Fragment C1 which is missing both the long arm and the globular end regions fo the short arms.

The fragment of laminin produced by cathespin G was purified by high-pressure liquid chromatography using a gel filtration column. The major fragment which eluted in the void volume was homogeneous as judged by 5% polyacrylamide gel electrophoresis under reducing conditions (gel not shown). The purified fragment was visualized by electron microscopy utilizing the rotary shadowing technique. Untreated laminin has the appearance of an asymmetric cross with one long arm (75 nm) and three identical short arms (37 nm) (FIG. 11). The fragment which represents the protease-resistant region of the laminin molecule retained three similar arms measuring a mean length of 32 nm (FIG. 11). Electron microscopy of the protease-resistant region of laminin remaining after chymotrypsin or plasmin digestion was similar to the fragment produced by cathepsin G. Thus, the protease-resistant fragment of laminin is composed of a major portion of the α subunit including the point where the three short arms intersect. The globular domains which were distinct in the intact laminin short arms were modified in the fragment. A short residual stump of the long arm was evident in most of the micrographs.

Although the three short arms of the laminin molecule are similar in appearance by electron microscopy, they may in fact have a different amino acid sequence. Following treatment of laminin with three types of proteases in the present report a T-shaped fragment is produced. When this fragment is studied without reduction of disulfide bonds it migrates as a single component with an apparent molecular weight of 350,000 on gel electrophoresis and sucrose gradient ultracentrifugation (data not shown). This same fragment when subjected to gel electrophoresis in the presence of a reducing agent migrates as two components of 130,000 and 160,000 $M_r$. The sum of the weights of these two components is in the range of 350,000. Evidently the two components are held together by disulfide bonds to form the cross-shaped structure.

Pepsin produced a fragment (called Pl) of laminin which is 290,000 $M_r$ prior to reduction (Hoppe-Seylers Z. Physiol. Chem. 361:1651–1660, 1980). However, after reduction this fragment migrates as a series of low-molecular-weight components. Thus pepsin produces many nicks in the molecule which are revealed after removal of disulfide bonds. In contrast to pepsin, the serine proteases described here produce specific limited fragments which are greater than 100,000 $M_r$ after reduction. Furthermore these major fragments are shown here to be derived from the α subunit of laminin. The marked difference in protease susceptibility of the two subunits of laminin support the concept that they are different gene products; in other words the 400-kd β subunit is not merely a dimer of the 200-kd α subunit. The limited digestion products greater than 100,000 $M_r$ produced by all three proteases are similar. Furthermore, the size or density of these fragments was not altered when the β subunit of laminin was removed with α-thrombin prior to digestion with cathepsin G, chymotrypsin, or plasmin. These fragments therefore represent a protease-resistant region of the α subunit. The β subunit of laminin is rapidly degraded into small fragments and the limited large-molecular-weight products obtained by certain neutral serine proteases are derived from the α subunit. These proteases recognize similar cleavage sites and produce identical fragments from the α subunit indicating that a specific region of this subunit is protease resistant. Since the length of the arms of the cathepsin G-derived fragment is shorter by about 5–6 nm than the short arms of the intact molecule, it is possible that the globular end regions are modified in size.

EXAMPLE II

Attachment Assays

A. Materials and Methods

1. Cell lines.

The MCF-7 human breast cancer cell line was provided by the Michigan Cancer Foundation. Characterization of the cells as to human and mammary origin has been summarized. The cells were shown to be invasive and to metastasize in nude mice. They were also invasive in vitro when human amnion connective tissue was used as a barrier.

The ZR-75-1 and T47-D human breast carcinoma lines were provided by L. Engel (Laboratory of Pathology, National Cancer Institute). These cells were verified to be carcinomas by electron microscopy criteria, to be human in origin by karyotypic analysis, and to contain mammary gland specific secretory milk proteins. Both of these lines grew poorly in nude mice with no gross metastases, even when subcutaneous xenotransplantation was performed in newborn nude mice. Normal human skin fibroblasts (CRL 1507 and CRL 1477) were obtained from the American Type Culture Collection.

2. Preparation of substrate, attachment factors, and laminin fragments.

Laminin fragments were prepared as described in Example I. Type I collagen was prepared from lathyritic rat skin (Biochemistry, 5: 3460–3473 (1966). Type IV collagen and laminin were prepared from the Engelbreth—Holm—Swarm tumor (FEBS Lett. 127: 257–262, (1981); and J. Biol. Chem., 254: 9933–9937, (1979). Laminin was iodinated by the lactoperoxidase method (Biochem. Biophys. Acta, 251: 363–369, 1969).

3. Attachment assay.

The assay was adapted fron Klebe as described by Terranova, et al. (Cell, 22: 719–728, 1980).

4. Cell binding.

Binding of laminin to MCF-7 and T47-D breast carcinoma cells and adult human fibroblasts CFL 1477 and CRL 1507 was performed with monolayer cell cultures. All cell lines were replica plated in multi-well culture dishes. (FB-6-TC, Limbro) in complete growth media. When the cells were 50–70%, the medium was changed to Dulbecco's modified Eagles's medium with 0.1% bovine serum albumin for a 2-hr. wash. The binding medium consisted of Dulbecco's modified Eagles's medium, 0.1% bovine serum albumin, and 20mM Hepes-buffer (pH 7.4). $^{125}$I-Labeled laminin ($^{125}$I-laminin) with either excess unlabeled laminin or excess unlabeled laminin fragments was added to 250 μl of phosphate-buffered saline (P$_1$/NaCl) to initiate the binding assay. After various times of incubation at 20° C. and 37° C. the binding medium was rapidly aspirated, and monolayers were washed three times with ice-cold P$_1$/NaCl containing 0.2% bovine serum albumin to remove unbound material. The cells were then removed by using 0.02% EDTA in P$_1$/NaCl and cell-bound radioactivity was determined in a Searle (Skokie, IL) Autogamma counter. Specific binding was defined as the total radioactivity bound minus the amount bound in the presence of a 100-fold excess of unlabeled material.

5. Collagen binding.

Procollagen type IV was dissolved in 0.5M acetic acid and neutralized with 0.05M Tris HCl/0.9M NaCl, pH 7.4. Five microliters of the solution (25 μg) was placed on a 13-mm SCWP nitrocellulose filter with 8-μm pore diameter (Millipore). The filters were then immersed in $P_1$/NaCl with 3% bovine serum albumin at 4° C. overnight. After washing, $^{125}$I-labeled laminin (1 mg/ml) or purified $^{125}$I-labeled laminin fragments were applied to the filters (10 μl) and incubated in a 100% relative humidity chamber for 20 min. After intensive washing in $P_1$/NaCl the bound radioactivity was quantitated with a gamma counter.

6. Rotary Shadowing and Electron Microscopy.

These techniques were performed according to the method of Engel, et al. modified as described in Rao, supra.

B. Results

1. Cell attachment to collagen.

When freshly trypsinized MCF-7, ZR-75-1, and T47-D cells were added to various substrates the MCF-7 cells preferred type IV collagen over type I collagen or plastic (data for types I and IV collagen shown in Table 2). In all experiments the MCF-7 cells attached more rapidly and to a greater extent to type IV collagen substrate compared to the ZR-75-1 and T47-D cell types. To determine whether the adherence of the cells to specific substrates was mediated by the presence of specific attachment factors, the effect of exogenous laminin and fibronectin on cell attachemnt to type I and type IV collagen, respectively, was tested. To eliminate the effect the endogenous synthesis of these factors might have on adherence, cells were treated with cycloheximide in the incubation media to inhibit protein synthesis. In the presence of cycloheximide, laminin stimulated the attachment of all three cell lines to type IV collagen. The MCF-7 cells showed an 8-fold stimulation by laminin compared to a 4-fold stimulation for the ZR-75-1 cells and 2-fold stimulation for the T47-D cells (FIG. 3). Fibronectin, when added to type I collagen in the presence of cycloheximide, caused a 7-fold increase in the attachment of the T47-D cells, a 5-fold increase in attachment of the ZR-75-1 cells, and only a 2-fold increase in the attachment of the MCF-7 cells (FIG. 3). These data indicate that the MCF-7 cells prefer type IV collagen as a substrate and use laminin as an attachment factor. Laminin in the same dose range failed to stimulate attachment of these cells to type I collagen (data not shown). In contrast, the T47-D cells utilized fibronectin to bind preferentially to type I collagen, whereas ZR-75-1 cells exhibited no preference for either laminin or fibronectin for attachment to type IV or type I collagen substrate, respectively.

2. Binding properties of laminin fragments.

In order to investigate which regions of the laminin molecule mediate the attachment of cells to type IV collagen, protease-derived fragments of laminin were tested for their attachment properties. α thrombin-derived α 3 fragment of laminin stimulated the attachment of MCF-7 cells to type IV collagen to the same extent as native laminin did (Table 1). The α 3 fragment is as active as a microgram basis, but it is less active than native laminin on a molar basis. The β component of laminin showed no attachment activity. The data supports the conclusion that the α 3 component of laminin contains the biologically active sites for both cell and collagen binding. The effect of the α 3 laminin component and a pepsin-derived "P1" $M_r$ 280,000 laminin fragment on the ability of the MCF-7 and T47-D cells to attach to type I and type IV collagen was measured in the presence of the native laminin molecule. The α 3 component stimulated adherence to type IV collagen, whereas the P1 fragment markedly inhibited attachment (Table 1). Neither fragment had an effect on attachment to type I collagen (data not shown). However, the T47-D cells attached to type IV collagen by utilizing laminin or laminin fragments to a much lesser degree (Table 1). A dose-response experiment using the P1 fragment is shown in FIG. 4. Attachment of both the MCF-7 cells and the T47-D cells to type IV collagen was completely inhibited by the P1 fragment at 1.0 μg/ml. A further laminin fragment ($M_r$ 350,000) produced by cathepsin G digestion (named "C1") completely inhibited the attachment of the MCF-7 cells to type IV collagen when used at concentrations of 1 μg/ml.

3. Laminin binding to cells.

If laminin mediates attachment of epithelial cells to type IV collagen, then these cells may possess specific surface receptors that are involved in recognizing laminin. Moreover, cells such as fibroblasts, which utilize fibronectin rather than laminin as an attachment factor, should lack these laminin-binding sites. Experiments were conducted to determine whether $^{125}$I-laminin binds to cells with high affinity and specificity. Binding of laminin to the MCF-7, T47-D, and the CFL 1477 and 1507 fibroblast cell lines was time dependent. Equilibrium binding was reached after 90 min. for all cell lines tested (FIGS. 4 and 5). The human fibroblast cell lines, CRL 1477 and 1507 showed no evidence of a specific laminin receptor (FIG. 5) whereas the epithelial T47-D cells exhibited a low lever of laminin binding when compared to the MCF-7 cells. Scatchard binding analysis (using MCF-7 cells) gave a roughly linear curve, with an estimated $K_d$ of 50-2.2 nM. Calculations suggest 10,000-100,000 binding sites per cell. The receptor for laminin could be extracted from the cell membrane by 0.1% Triton X-100 and had a molecular weight of 60,000-75,000 after isolation by laminin affinity chromatography. Laminin fragments α 3 and P1 both competed for $^{125}$I-laminin, binding at a level similar to whole laminin (FIG. 4). Laminin bound to both attached and suspended MCF-7 cells. For the latter, binding was identified 2 hr. after trypsinization followed by incubation in Dulbecco's modified Eagle's medium containing 0.5% bovine serum albumin. Heat-denatured laminin and fibronectin were 1/50th to 1/500th as effective as native laminin in competing for $^{125}$I-laminin binding. Both $^{125}$I-laminin and $^{125}$I-labeled α 3 laminin fragment maintained biological activity when used in an attachment assay. Therefore, a major domain of the laminin molecule that binds to the MCF-7 and T47-D cells is retained on both the α 3 laminin component and the C1 or P1 laminin fragment (FIG. 4, Table 1).

4. Laminin binding to collagen.

In contrast, the same laminin fragments (α 3 and P1) showed a marked difference in their ability to bind to type IV collagen immobilized on nitrocellulose. Native laminin and the α 3 fragment bound equally well to type IV collagen (Table I). The P1 or C1 fragments exhibited no capacity to bind to type IV collagen (Table I). The structural and binding properties of the various laminin fragments are summarized in FIG. 1.

EXAMPLE III

Isolation of Tumor Cell Laminin Receptor.

A. Materials and Methods

Metastatic BL6 melanoma cells were supplied by Dr. Ian Hart, Frederick Md. The growth and attachment properties of these tumor cells have been described. BL6 cells were cultivated in RPMI 1640 media supplemented with 10% FCS. Plasma membranes were isolated from cells in log phase of growth (*J. Biol. Chem.*, 255 1722–1731, 1980). The plasma membrane homogenate was solubilized in 0.1% Triton X 100, 1.0–2.0 mg protein/ml. After centrifugation at 30,000 g for 45 min., the supernate was collected and incubated with SM2 Biobeads (Bio-Rad) to remove the Triton. Iodination of the laminin ligand and the plasma membrane extract was performed using the lactoperoxidase method, supra. Laminin receptors were measured on living cells in suspension. After trypsinization the BL6 cells were incubated in complete media under constant agitation at 37° C. for 2 hr. The labeled ligand plus 250 fold excess unlabeled ligand was added and the incubation was continued for 2 hours at 25° C. The cell-bound and free ligand was separated by centrifugation. Binding assays on plasma membrane extracts were performed using one member of the ligand or receptor pair bound to solid phase nitrocellulose Millipore SCWP circles (Terranova, et al., supra) or cyanogen bromide activated Sepharose 4B. In the latter case, 25 µg of laminin or plasma membrane extract protein bound to cyanogen bromide activated Sepharose 4B (100 µl) was mixed with an equal amount of 25mM Tris, 5mM MgCl$_2$ and CaCl$_2$, pH 7.4 and 100 µl of this buffer containing 0.1% BSA. $^{125}$I-labeled plasma membrane extract ($10^8$ cpm/mg) or $^{125}$I-labeled laminin ($10^9$ cpm/mg) was added in a total volume of 100 µl, diluted with the buffer. Competition was performed with various concentrations of unlabeled laminin in solution or unlabeled plasma membrane extracts (2 to 20 µg). The binding assay mixture was incubated at 4° C. over-night. The laminin-Sepharose beads were collected by centrifugation at 5,000 rpm for 30 min. and the pellet was washed twice with 2.0 ml of the buffer containing 0.1% BSA. The proteins in the first spin supernate and the pellet were identified by electrophoresis on 7% slab gels by the method of Laemmli, followed by autoradiography. Laminin affinity chromatography was performed using purified laminin cross linked to Sepharose 4B. $^{125}$I-labeled plasma membrane extract was incubated 15 hrs. in the laminin-Sepharose affinity column (1×15 cm) at 4° C. The unbound radio-activity was washed with 40 ml of 25mM Tris, 5mM CaCl$_2$, 5mM MgCl$_2$, 0.9% NaCl, pH 7.4. The neutralized with 1.0 Tris saline, and lyophilized. The proteins were identified by slab gel electrophoresis and autoradiography. The number of laminin receptor sites and the kd were calculated by Scatchard analysis.

B. Results

Figure 7A:
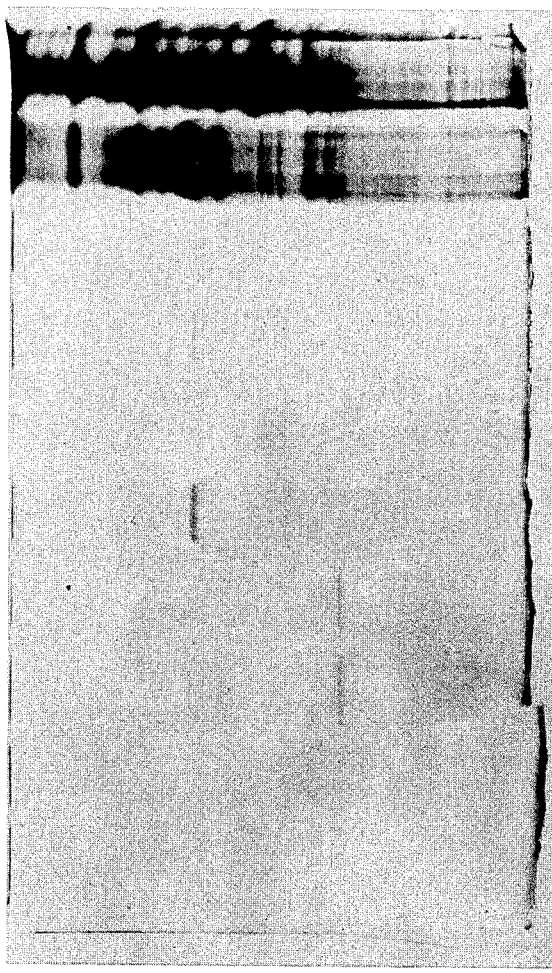
FIG. 7 shows SDS (7%) gel electrophoresis autoradiography demonstrating binding of solubilized 125 I-labeled BL6 plasma membrane extract to laminin immobilized on Sepharose 4B. A: plasma membrane extract. B: supernate fraction of extract unbound to laminin-Sepharose. C and D: replicate pellet fraction of extract bound to laminin-Sepharose. E: pellet fraction after competition with 250×) unlabeled plasma membrane extract. F: pellet fraction after competition with laminim (250×) in solution. A single major component (denoted with the arrow) binds to the solid phase laminin and is removed by competition.

BL6 melanoma cells exhibited saturable binding for laminin. Scatchard analysis demonstrated approximately 110,000 binding sites per cell with a high affinity: kd=2.2 nm (FIG. 6A). Laminin binding to the tumor cells was abolished by trypsinization. The receptor regenerated after 2 hrs. of cell incubation in serum free or serum containing media. Collagen, denatured laminin, fibronectin or serum did not compete for binding. Binding of $^{125}$I-laminin to isolated cell plasma membranes also showed a high affinity: kd=1.5 nm (FIG. 6B). Excess unbound laminin competed for binding of the solubilized membrane receptor to laminin immobilized to a solid phase (FIG. 7). Gel electrophoresis of the solubilized membrane proteins bound to laminin before and after competition demonstrated a single molecule weight class for the receptor (FIG. 7). Laminin affinity chromatography was therefore used to isolate the receptor (FIG. 8 and FIG. 7a) with a 900 fold purification relative to the crude membrane extract. The receptor molecular weight was 67,000 after reduction by polyacrylamide gel electrophoresis. The isolated receptor retained a high binding affinity for laminin: kd=2 nm (FIG. 6C).

EXAMPLE IV

Measurement of Laminin Receptors in Human Breast Carcinoma Cells

A. Materials and Methods

1. Preparation of Membranes.

Human breast cancer tissue samples were obtained at the time of mastectomy for biopsy proven infiltrating duct carcinoma. The tissues were frozen in liquid nitrogen and pulverized. The pulverized tissue was diluted in a volume ratio of 1 to 4 in 25mM Tris 0.3M sucrose pH 7.4, and homogenized using a polytron at 0° C. The homogenate was centrifuged 15,000 g for 20 minutes. The fat layer was discarded and the supernatant was removed and centrifuged at 100,000 g 4° C. for 60 minutes. The pellet was suspended in a 25mM Tris buffer containing 1.5mM MgSO$_4$ and 0.15mM Ca Cl$_2$ pH 7.4. This membrane preparation was diluted to 100 mg/100 µl.

2. Binding Assay

Laminin or laminin fragments were purified and iodinated as described previously. The binding assay was conducted at room temperature for 90 min. using 100 µl of the membrane fraction and $^{125}$I-laminin with a specific activity of 70,000 cpm per $2.3 \times 10^{-9}$M. Specific binding was determined by using cold competitor ligand at a 10,000 fold excess concentration. The bound and free ligand was separated by centrifugation at 5,000 g for 30 minutes.

B. Results

Figure 9:
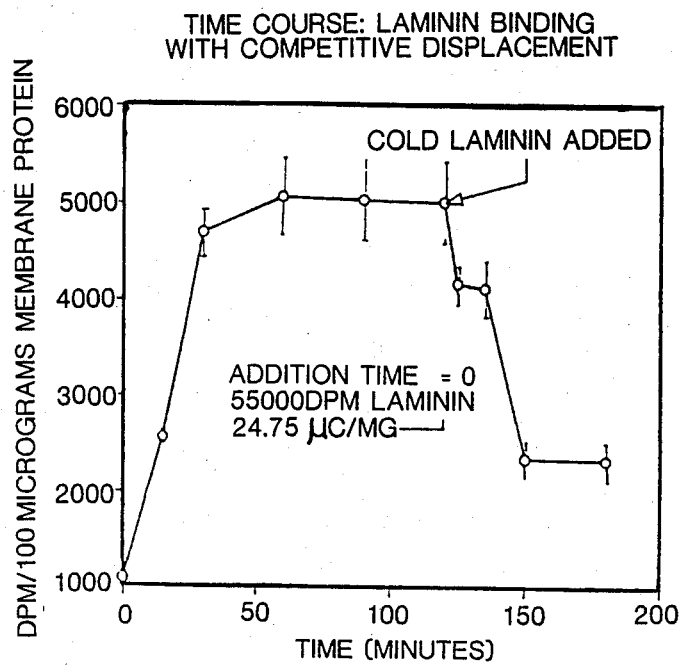
FIG. 9 shows tissue course of 125-I-Laminin binding to human breast carcinoma plasma membranes at 25° C. The plateau of binding is reached by one hour. With the addition of cold ligand rapid displacement is noted. The error bars indicate the range of quadruplicate assays from 10 pooled patient samples.
Figure 10:
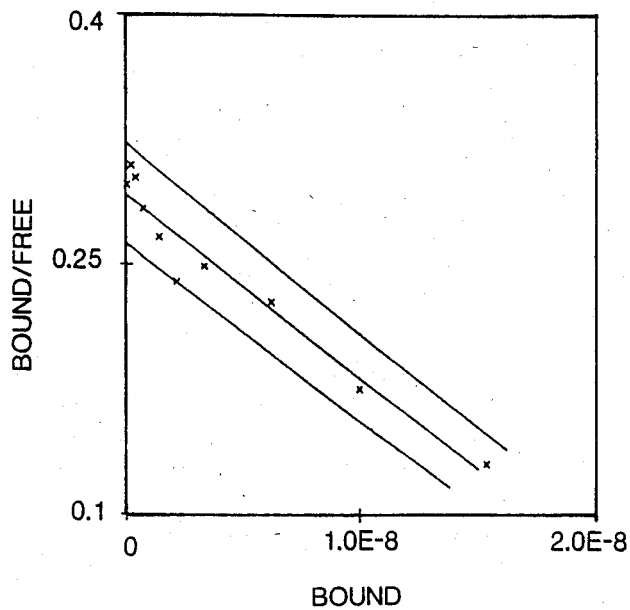
FIG. 10 shows scatchard analysis of specific laminin binding to human breast carcinoma plasma membranes. R=0.85. The Kd is in the range of 2 nm.

Plasma membrane fractions from human breast cancer tissue exhibited saturable binding of laminin in time course studies (FIG. 9). The plateau of binding was reached at one hour (25° C.). After the plateau phase of binding was established, the addition of 1,000 fold excess cold ligand rapidly displaced the labeled ligand. Scatchard analysis of the specific binding was linear consistent with a single class of binding sites (r=0.85) (FIG. 10). No specific binding was noted in samples from mammary fibrosclerosis tissue containing no neoplastic cells. Heat denaturation of the membrane fraction abolished binding activity. Fibronectin, epidermal growth factor, or serum did not compete for binding. The use of purified fragments of the laminin molecule (FIG. 11) enabled us to identify the domains of laminin participating in its various binding functions. Whole laminin appears as a four armed cross by rotary shadowing electron microscopy (FIG. 11). The fragment which lacks the long arm contains full binding activity for the laminin receptor, mediates cell attachment, and binds to type IV collagen, while the fragment which lacks the long arm and the globular end regions of the short arms competes for specific binding to the receptor with an affinity equal to whole laminin.

EXAMPLE V

Preparation of Antibodies to the Laminin Cell Receptor

Antibodies to the receptor purified according to Example II were raised in New Zealand white rabbits by three injections of isolated receptor (250 μg per injection) emulsified in Freud's complete adjuvant. The specificity of the antibody was verified by standard solid phase immunoassay. The antibody is radiolabelled, and employed in a conventional radioimmunoassay for laminin receptor.

EXAMPLE VI

In vivo Therapy with Cl Laminin Fragment

Figure 12:
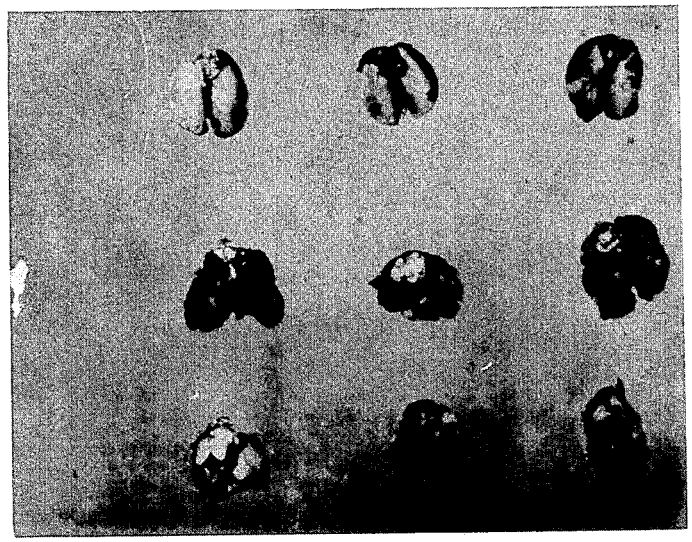
FIG. 12 shows results of treatment with C1 fragment at two different levels (1 mg and 10 mg per ml) compared to untreated (control) metastases.

BL6 murine melanoma cells (Example III) were preincubated for three hours with laminin Cl fragment (obtained as in Example I) at concentrations of 1 mg Cl per ml cells, and 10 mg. Cl per ml cells. The incubated cells were harvested, and administered in vivo to nude mice according to standard mouse protocols. The three control mice and six treated mice were sacrificed after 3 weeks, and the lungs examined. The control lungs showed a large number of metastases; the lungs of the three mice treated with Cl at 1 mg/ml showed a reduced number of matastases, and the lungs of the three mice treated with Cl at 10 mg/ml were substantially free from metastases. The experiment was repeated seven times with comparable results. A representative photograph of the lungs from one experiment is set forth in FIG. 12.

What is claimed is:

1. An isolated receptor having specific binding affinity for laminin.

2. The receptor of claim 1 being purified and having a molecular weight of about 50,000 to about 75,000.

3. A method for evaluating the effectiveness of a chemotherapeutic agent for treating cancer cells expressing the receptor of claim 1, comprising interacting a conjugate of the agent and a ligand specific for said receptor with a population of carcinoma cells prior and after chemotherapy.

4. A laminin fragment having a binding domain for the receptor of claim 1 without having a binding domain for type IV collagen.

5. The receptor of claim 1 complexed with a ligand comprising laminin, a laminin fragment having a binding domain for the receptor, or an antibody to the receptor.

6. A method for inhibiting attachment to type IV collagen of cells having the receptor of claim 1 comprising blocking the receptor site of said cells with a laminin, a laminin fragment having a binding domain for the cell receptor without having a binding domain for type IV collagen, a ligand having specificity against said receptor, or an analogue thereof.

7. The method of claim 6, wherein the cells are human breast carcinoma cells.

8. A method for separating metastatic cancer cells expressing the cell receptor of claim 1 from a mixed population of cells comprising binding the metastatic cancer cells to a ligand having a binding domain for the cell receptor, and separating bound from unbound cells.

9. The method of claim 8, wherein the ligand is laminin or a laminin fragment obtained by digestion of laminin with a proteolytic enzyme.

10. An antibody being specifically reactive to receptor of claim 1.

11. A method for detecting the presence of human breast carcinoma comprising reacting a sample of a tissue suspected to have said carcinoma with antibody of claim 10 and determining binding between said tissue and the antibody.

12. The method of claim 11 wherein said sample is a plasma membrane fraction.

13. The method of claim 12 determining said binding by radioimmunoassay wherein said antibody is radiolabelled.

14. A method for localizing a chemotherapeutic agent on the surface of cancer cells expressing the receptor of claim 1, comprising conjugating the agent with a ligand specific for the cell receptor, and interacting the conjugate with said cells.

15. The method of claim 14, wherein the ligand is an antibody for the receptor.

16. The method of claim 14, wherein the cancer cells are human breast carcinoma cells.

17. The method of claim 14, wherein the ligand is laminin or a laminin fragment having a binding domain for said receptor.

18. A therapeutic composition of inhibiting growth of carcinoma cells having the receptor of claim 1, comprising a pharmaceutically acceptable carrier and growth inhibiting amount of a ligand having specificity against said cells.

19. The therapeutic composition of claim 18, wherein said ligand is selected from the group consisting of laminin, a laminin fragment and an antibody having specificity against said receptor.

20. The therapeutic composition of claim 18, wherein the laminin fragment lacks a binding domain for type IV collagen.

21. The therapeutic composition of claim 18, wherein the laminin fragment includes a binding domain for type IV collagen.

22. A kit for detecting the presence of metastasizing cancer cells having the receptor of claim 1, comprising a container containing a ligand selected from the group consisting of laminin, a laminin fragment having a binding domain for the cell receptor and an antibody having specificity for the receptor.

23. The diagnostic kit of claim 22, wherein the laminin fragment is the digestion product of laminin and chymotrypsin, cathepsin G, or plasmin.

24. The kit of claim 22, wherein the ligand is radiolabelled.

25. The kit of claim 24 wherein the kit further comprises an unlabelled ligand which competes with the labelled ligand for binding to the cell receptor.

26. The kit of claim 24 wherein the labelled ligand is an antibody to the cell receptor.

* * * * *